United States Patent [19]

Powell

[11] Patent Number: 4,802,478
[45] Date of Patent: Feb. 7, 1989

[54] MEDICAL STAPLE AND REMOVAL METHOD

[75] Inventor: August L. Powell, Livonia Township, Sherburne County, Minn.

[73] Assignee: Minnesota Mining and Manufacturing Company, St. Paul, Minn.

[21] Appl. No.: 647,256

[22] Filed: Aug. 31, 1984

Related U.S. Application Data

[63] Continuation of Ser. No. 354,764, Mar. 4, 1982, abandoned.

[51] Int. Cl.[4] .............................................. A61B 17/04
[52] U.S. Cl. ............................ 128/334 R; 227/DIG. 1
[58] Field of Search ................... 128/335, 334 R, 325; 227/DIG. 1, DIG. 1 C

[56] References Cited

U.S. PATENT DOCUMENTS

| | | | |
|---|---|---|---|
| 2,111,404 | 3/1938 | Pankonin | 411/457 |
| 4,127,227 | 11/1978 | Green | 411/457 |
| 4,206,520 | 5/1977 | Rothfuss | 254/28 |
| 4,256,251 | 3/1981 | Moshofsky | 227/DIG. 1 |
| 4,317,535 | 3/1982 | Huftel | 128/334 R |
| 4,375,866 | 3/1983 | Giersch | 227/DIG. 1 |
| 4,399,810 | 8/1983 | Samuels et al. | 128/335 |
| 4,505,273 | 3/1985 | Braun et al. | 128/335 |

*Primary Examiner*—C. Fred Rosenbaum
*Assistant Examiner*—Gene B. Kartchner
*Attorney, Agent, or Firm*—Donald M. Sell; William L. Huebsch

[57] ABSTRACT

A method for bending a staple closed in living tissue so that its pointed ends pierce the tissue, and for subsequently opening the staple by bending the central portion of the staple to generally a U-shape so that the staple end portions retract from the tissue through the use of a staple remover. The central portion of the staple has a crank-like structure adapted to receive jaw members of the staple remover, and in reponse to pressure from the jaw members to first orient the staple at a predetermined position with respect to the jaw members, and to then maintain that orientation as the staple is bent open.

5 Claims, 2 Drawing Sheets

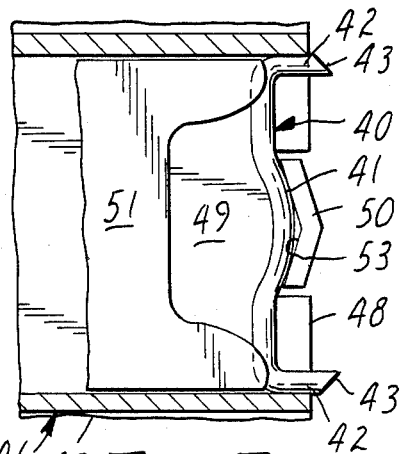 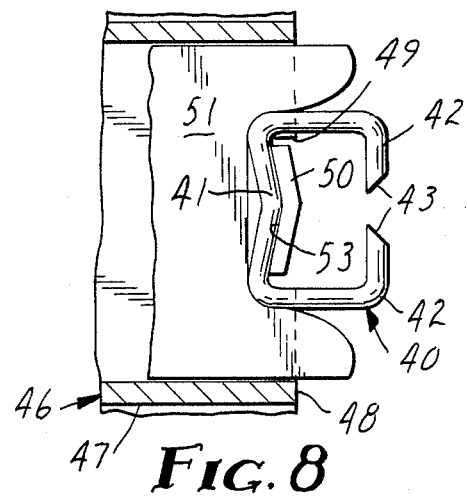 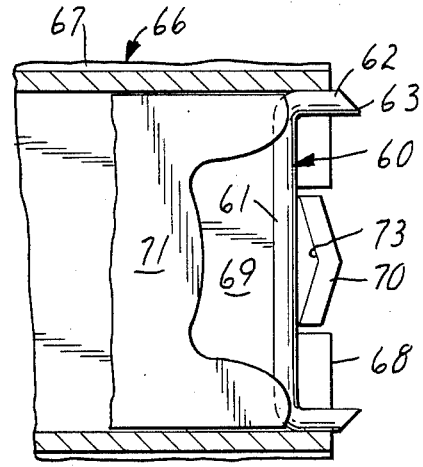 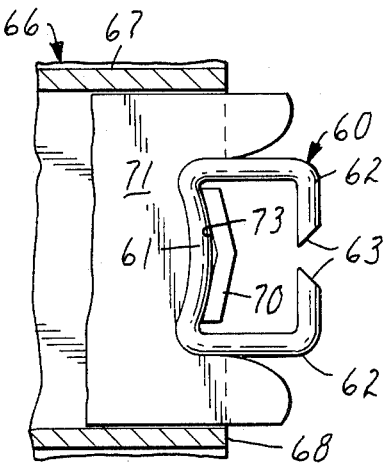 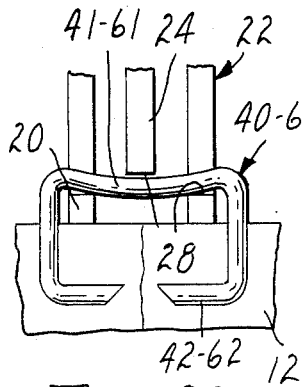 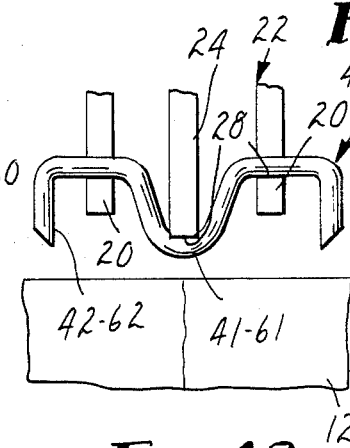 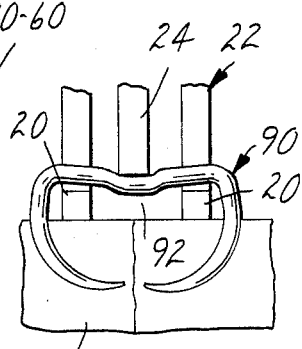

MEDICAL STAPLE AND REMOVAL METHOD

This is a continuation of application Ser. No. 354,764 filed on Mar. 4, 1982, now abandoned.

TECHNICAL FIELD

This invention relates to methods for removing staples which have been inserted to close openings in living tissue such as skin, and to staple shapes that facilitate such removal.

BACKGROUND ART

A prior art method relevant to the present invention for inserting and removing staples with respect to living tissue is well known in the art. Generally that method includes (1) providing an open staple comprising a central portion and end portions attached to the central portion that have pointed distal ends which project generally normally away from its central portion in a single plane; (2) positioning the pointed ends of the staple adjacent the tissue; (3) closing the staple by bending it in the plane so that its pointed ends pierce the tissue and its end portions move to a position with their pointed ends adjacent each other directed toward, aligned with and adjacent each other so that the end portions and the central portion of the staple define a generally "D" shaped single loop and so that the tissue is gathered and held together by the closed staple; and then (4) opening the staple by bending the central portion of the staple to generally a U-shape so that the end portions of the staple will retract from the tissue, which bending is caused by placing two spaced jaw members of a staple remover between the tissue and the central portion of the staple, placing a third jaw member of the staple remover between the two spaced jaw members on the side of the central portion opposite the tissue, and manually manipulating the staple remover to move the third jaw member through the two spaced jaw members so that the U-shape bend is made in the central portion of the staple.

With this prior art method, if the end portions of the staple do not remain in the same plane when the staple is bent open, the staple end portions will tear a new opening through the tissue rather than being retracted generally along the opening in the tissue they occupied when the staple was closed. The staple will be bent open with its end portions remaining in the same plane only if the jaws of the staple remover contact the central portion of the staple on its surfaces disposed at right angles to the plane of its closed end portions. It is often difficult for a user to be certain that he has engaged the staple remover on these surfaces of the staple's central portion, however, since the central portion of the staple is typically round and gives no indication of its orientation; and since the end portions of the closed staple are often buried in the tissue where their orientation cannot be determined. Also, even if the orientation of the buried end portions of the staple can be determined to be at some angle other then 90 degrees to the surface of the tissue, it is often difficult to properly engage the jaws of the remover on surfaces of the central portion without pressing the end portions of the jaws into the tissue, which can cause damage.

DISCLOSURE OF INVENTION

The present invention allows staples to be consistently bent open so that the central portions of the staple remain in the same plane and minimum damage is done to the tissue, even if the end portions of the staples cannot be seen in the tissue and are disposed at an angle of other than 90 degrees with respect to the surface of the tissue.

The method according to the present invention is an improvement over the prior art method described above in that it further includes forming the central portion of the staple into a crank-like structure adapted to receive and be operated by the jaw members so that in response to pressure from the jaw members as they are initially pressed against the central portion the crank-like structure will first orient the staple at a predetermined position with respect to the jaw members with the surfaces of the jaws contacting surfaces of the central portion oriented at right angles to the planes of the end portions of the staple, and will then maintain that orientation as the central portion is bent to generally a U-shape by subsequent relative movement of the jaw members.

Thus, even though the end portions of the staple are buried and obscured in tissue, when the jaws of the staple remover are engaged and first pressed against the central portion of the staple, a force will first be applied that can be felt by the person removing the staple to rotate the jaws and staple into the proper angular relationship with each other, and the user can pivot the staple remover to minimize sidewise movement of the staple's end portions within the tissue so that the staple can be extracted with minimum tissue damage.

The crank-like structure is preferably formed by providing a slight V-shaped bend across the entire width of the central portion of the staple in the plane of its end portions, but can also be provided by forming indentations only slightly wider than jaws of the staple remover to receive one or more of the jaws; and may either be formed in the staple when it is manufactured or by a stapler when the staple is bent closed.

BRIEF DESCRIPTION OF DRAWING

The present invention will be more thoroughly described with reference to the accompanying drawing wherein like numbers refer to like parts in the several views and wherein:

FIGS. 7 and 8 are fragmentary views sequentially illustrating steps in the method according to the present invention for closing a staple of a different shape from the staple of FIG. 1 through the use of a stapler of a different structure from the stapler of FIG. 1;

FIGS. 9 and 10 are fragmentary views sequentially illustrating steps in the method according to the present invention for closing a staple of a slightly different shape from the staple of FIG. 7 through the use of a stapler of a slightly different structure from the stapler of FIG. 7;

FIGS. 11 and 12 are enlarged front views illustrating steps in the method according to the present invention for opening the closed staples of FIGS. 8 and 10; and FIG. 13 is a front view illustrating steps in the method according to the present invention for initiating removal of a staple having a different structure from the stapler illustrated in the other Figures by engaging the staple remover with the staple.

DETAILED DESCRIPTION

Figure 1:
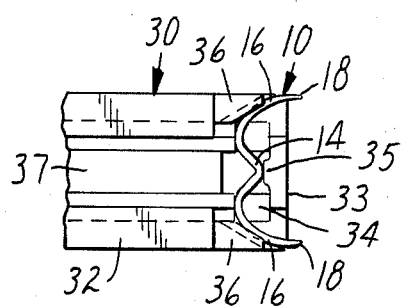
FIGS. 1 and 2 are fragmentary views sequentially illustrating steps in the method according to the present invention for closing a staple in living tissue through the use of a stapler.
Figure 2:
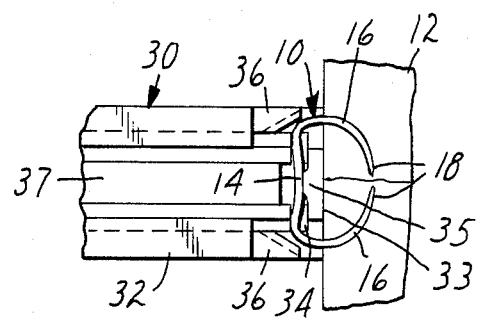
Figure 3:
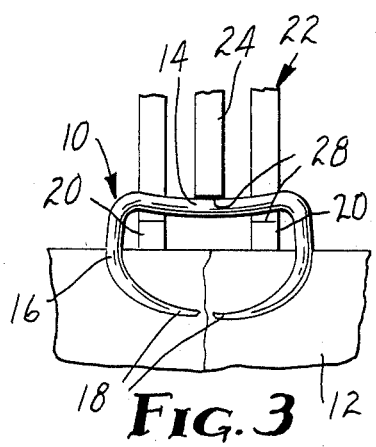
FIG. 3 is an enlarged front view illustrating steps in the method according to the present invention for initiating removal of the staple of FIG. 2 from the living tissue by engaging a staple remover with the staple.
Figure 4:
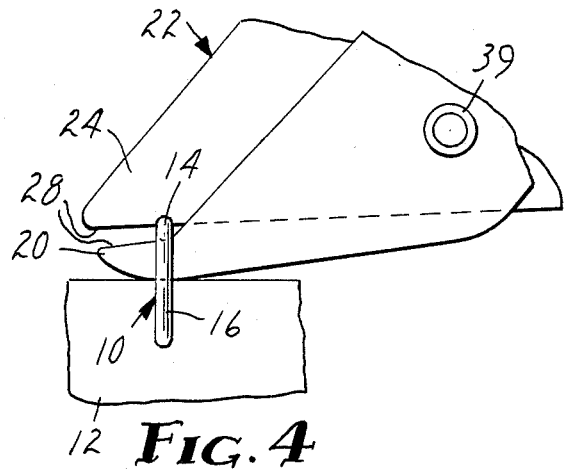
FIG. 4 is a fragmentary side view of the staple, staple remover and living tissue as shown in FIG. 3.
Figure 5:
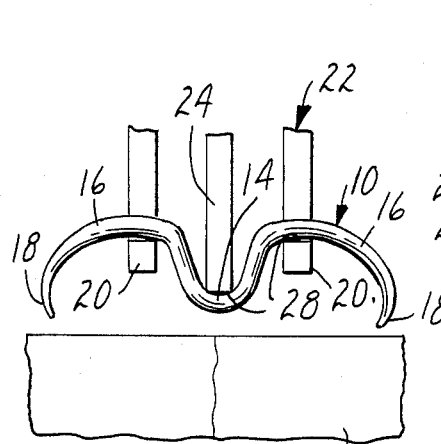
FIG. 5 is a front view of the staple, staple remover and living tissue shown in FIGS. 3 and 4 after the staple has been opened via the staple remover of FIG. 3.
Figure 6:
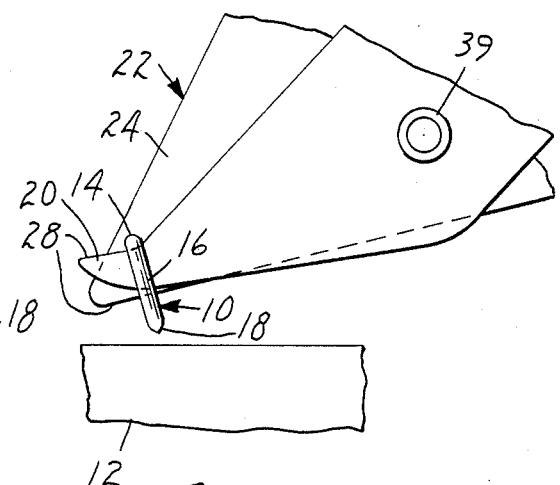
FIG. 6 is a fragmentary side view of the staple remover, staple and living tissue as shown in FIG. 5.

Referring now to FIGS. 1 through 6 of the drawing, there are illustrated various steps in a method according to the present invention for inserting and removing a staple 10 with respect to living tissue or skin 12, and a novel shape for the staple 10 that facilitates that method.

Generally, in common with known prior art methods, the method according to the present invention includes (1) providing the open staple 10 which staple 10 comprises a central portion 14 and end portions 16 attached to the central portion 14 that have pointed distal ends 18 which project generally normally away from its central portion 14 in the same plane as its central portion 14 (FIG. 1); (2) positioning the pointed ends 18 of the staple 10 adjacent the tissue 12; (3) closing the staple 10 by bending it so that its pointed ends 18 pierce the tissue 12 and its end portions 16 move to a position with their pointed ends 18 adjacent each other directed toward, aligned with and adjacent each other so that the end portion 16 and the central portion 14 of the staple 10 define a generally "D" shaped single loop and so that the tissue 12 is gathered and held together by the closed staple 10 (FIG. 2); and then (4) opening the staple 10 by bending the central portion 14 of the staple 10 to generally a U-shaped so that the end portions 16 of the staple 10 will retract from the tissue 12, which bending is caused by placing two spaced jaw members 20 of a staple remover 22 between the tissue 12 and the central portion 14 of the staple 10, placing a third jaw member 24 of the staple remover 22 on the side of the central portion 14 opposite the tissue 12 (FIGS. 3 and 4), and manually manipulating the staple remover 22 to move the third jaw member 24 through and into general alignment with the spaced jaw members 20 (FIGS. 5 and 6) so that the U-shape bend is made in the central portion 14.

Unlike such prior art methods, however, the method according to the present invention further includes forming the central portion 14 of the staple 10 into a crank-like structure that is adapted to receive the jaw members 20 and 24, and, in response to pressure from the jaw members 20 and 24 as they are initially pressed against the central portion 14 of the staple 10, will orient the staple 10 at a predetermined position with respect to the jaw members 20 and 24 with the opposed planar surfaces 28 of the jaws 20 and 24 contacting opposite surfaces of the central portion 14 at right angles to the plane of the central and end portions 14 and 16, and will cause that orientation to be maintained as the central portion 14 is bent to generally a U-shape by the subsequent relative movement of jaw members 20 and 24.

The crank-like structure in the central portion 14 of the staple 10 is provided by causing the central portion 14 of the closed staple 10 to have a slight V-shape in the plane of the end portions 16 of the staple 10, with the point of the V between and adjacent the pointed ends 18. When the staple remover 22 is engaged with the central portion 14, its third jaw member 24 will move into the depression at the middle of the stapler central portion 14 opposite the point of the V, the central portion 14 will be journaled on the spaced jaw members 20 adjacent the end portions 16 of the staple, and the parts of the central portions between the spaced jaw members 20 and the central jaw member will serve as crank arms to first rotate the staple 10 to the position indicated above as pressure is first applied by the jaw members 20 and 24; and to then maintain that orientation as the central portion 14 is bent to generally a U-shape to open the staple 10.

The staple 10 is of a type more fully described in U.S. Pat. No. 4,185,762 (the content whereof is incorporated herein by reference) which has a sharp V-shaped bend across its entire central portion 14 when it is manufactured. The staple 10 is then inserted in a stapler 30 (FIGS. 1 and 2) of the type described in U.S. patent application Ser. No. 299,068 (the disclosure whereof is incorporated herein by reference), which stapler 30, like other prior art staplers, includes an elongate body 32 having a front end 33, a guide surface 34 adjacent its front end 33, and an anvil 35 transversely centered at its front end 33 projecting at a right angle to the guide surface 34; means including undercut projections 36 for positioning the side surface of the staple 10 on the body 32 adjacent the anvil 35 with the side surface of the staple 10 along the guide surface 34 and the pointed ends 18 of the staple 10 adjacent the front end 33 of the body 32; a ram 37 having an end surface adapted to engage the edge surface of the staple 10 opposite its pointed end portions 16; means mounting the ram 37 on the body 32 for movement from an open position (FIG. 1) with the end surface of the ram 37 spaced from the anvil 35 to afford space for the open staple 10 therebetween to a closed position (FIG. 2) to cause the end surface of the ram 37 to engage and bend the staple 10 closed around the anvil 35; and means (not shown) for affording manual movement of the ram 37 to its closed position to close the staple 10. Such movement of the ram 37 to its closed position will straighten the bend in the generally V-shaped central portion of the staple so that the points 18 and end portions 16 of the staple (which are arcuate) enter the tissue 12 positioned adjacent the points 18 of the staple 10. The movement of the ram 37, however, is limited so that the central portion 14 of the staple 10 will retain a slight V-shape (e.g., an included angle of less than about 174 degrees and preferably about 170 degrees after the staple 10 is closed to provide the crank-like structure in the central portion 14 of the staple 10 for the purpose described above).

The staple remover 22 used to subsequently remove the staple 10 (FIGS. 3 through 6) is commercially available as part No. SR-1 from the Surgical Products Division of Minnesota Mining and Manufacturing Company, St. Paul, Minn., 55144. The spaced jaw members 20 and the jaw member 24 are mounted for relative pivotal movement about a rivet 39 which also holds them together, and are disposed at the end of handles having manually engageable portions (not shown) that afford manipulating the jaw members to open a staple, as is well known in the art.

Referring now to FIGS. 7 through 13 of the drawing, there are illustrated various alternatives for performing the steps in the method according to the present invention for inserting and removing staples with respect to living tissue or skin, and alternate novel shapes for staples that can be used in that method.

As is shown in FIGS. 7 and 8, the method according to the present invention can utilize a staple 40 which, when open (FIG. 7), has a central portion 41 with a slight V-shaped bend across its entire width formed when the staple 40 is manufactured to provide a crank-like structure for properly orienting the closed staple 40 between the jaw members 20 and 24 of the staple remover 22, and generally L-shaped end portions 42 attached to the central portion 41 that have pointed distal ends 43. Such a staple 40 can be bent closed through the use of a stapler 46 generally of the type described in U.S. Pat. No. 4,202,480, (the disclosure whereof is incorporated herein by reference). The stapler 46, like the stapler 30, includes an elongate body 47 having a front end 48, a guide surface 49 adjacent its front end 48, and an anvil 50 transversely centered at its front end 48 projecting at a right angle to the guide surface 49; means for positioning the side surface of the staple 40 on the body 47 adjacent the anvil 50 with the side surface of the staple 40 along the guide surface 49 and the pointed ends 43 of the staple 40 adjacent the front end 48 of the body 47; a ram 51 having an end surface adapted to engage the edge surface of the staple 40 opposite its pointed ends 43; means mounting the ram 51 on the body 47 for movement from an open position (FIG. 7) with the end surface of the ram 51 spaced from the anvil 50 to afford space for the open staple 40 therebetween to a closed position (FIG. 8) to cause the end surface of the ram 51 to engage and bend the staple 40 closed around the anvil 50; and means (not shown) for affording manual movement of the ram 51 to its closed position to close the staple 40. Such movement of the ram 51 to its closed position will bend the staple 40 between its central portion 41 and its end portions 42 so that its L-shaped end portions 42 enter tissue or skin positioned adjacent their pointed ends 43. The stapler 46 is modified from the stapler described in U.S. Pat. No. 4,202,480, however, in that a surface 53 of the stapler's anvil 50 engaged by the central portion 41 of the staple 40 has a slight V-shape generally corresponding to the shape of the central portion 41 of the staple 40 so that the central portion 41 of the staple 40 will retain its slight V-shape after the staple 40 is closed to provide the crank-like structure for the purpose described above.

Alternatively, as is shown in FIGS. 9 and 10, the method according to the present invention can utilize a staple 60 that, when open (FIG. 9), has a straight central portion 61 and generally L-shaped end portions 62 attached to the central portion 61 that have pointed distal ends 63. Such a staple 60 can also be bent closed (FIG. 10) through the use of a stapler 66 generally of the type described in U.S. Pat. No. 4,202,480 which, like the stapler 46, includes an elongate body 67 having a front end 68, a guide surface 69 adjacent its front end 68 projecting at a right angle to the guide surface 69; means for positioning the side surface of the staple 60 on the body 67 adjacent the anvil 70 with the side surface of the staple 60 along the guide surface 69 and the pointed ends 63 of the staple 60 adjacent the front end 68 of the body 67; a ram 71 having an end surface adapted to engage the edge surface of the staple 60 opposite its pointed ends 63; means mounting the ram 71 on the body 67 for movement from an open position (FIG. 9) with the end surface of the ram 71 spaced from the anvil 70 to afford space for the open staple 60 therebetween to a closed position (FIG. 10) to cause the end surface of the ram 71 to engage and bend the staple 60 closed around the anvil 70; and means (not shown) for affording manual movement of the ram 71 to its closed position to close the staple 60. Such movement of the ram 71 to its closed position will bend the staple 60 between its central portion 61 and its end portions 62 so that its L-shaped end portions 62 enter tissue positioned adjacent their pointed ends 63. Like the stapler 46, the stapler 66 is modified from the stapler described in U.S. Pat. No. 4,202,480, in that a surface 73 of the stapler's anvil 70 adjacent the central portion 61 of the staple has a slight V-shape, and additionally that the portion of the ram 71 adjacent the anvil 70 has a corresponding slight V-shape so that the central portion 61 of the staple will be bent to a slight V-shape between the ram 71 and anvil 70 as the staple 60 is closed to provide the crank-like structure therein for the purpose described above.

Whether the staple 40 is closed as shown in FIGS. 7 and 8 or the staple 60 is closed as shown in FIGS. 9 and 10, the resultant closed staple 40 or 60 may then be opened as is shown in FIGS. 11 and 12, by placing the two spaced jaw members 20 of the staple remover 22 between the tissue 12 and the central portion 41 or 61 of the staple 40 or 60, placing the third jaw member 24 of the staple remover 22 on the side of the central portion 41 or 61 opposite the tissue (FIG. 11), and manually manipulating the staple remover 22 to move the jaw member 24 through the jaw members 20 (FIG. 12) so that a U-shape bend is made in the central portion 41 or 61 and the end portions 42 or 62 of the staple 40 or 60 retract from the tissue 12. During such opening of the staple 40 or 60 the crank-like structure in its central portion 41 or 61 caused by its slight V-shape causes the staple 40 or 60 to first become oriented at a predetermined position with respect to the jaw members 20 and 24 with the opposed planar surfaces 28 of the jaws 20 and 24 contacting opposite surfaces of the central portion 41 or 61 oriented at right angles to the plane of the central and end portions 41, 42 or 61, 62 and causes that orientation to be maintained as the central portion 41 or 61 is bent to generally a U-shape by the subsequent relative movement of the jaw members 20 and 24.

The present invention has now been described with reference to several staple and stapler structures with which it may be practiced. It will be apparent to those skilled in the art that many other staple and stapler structures may be utilized without departing from the spirit of the invention. For example, as shown in FIG. 13, a staple 90 may have a narrow offset 92 on its central portion 94 in the plane of its end portion formed when the staple 90 is manufactured, or formed by a stapler when the staple 90 is closed, which offset 92 is adapted to receive the central jaw member 24 of the staple remover 22 to orient the staple relative thereto for proper opening. Alternatively, other crank-like structures that provide that orientation may be provided such as by flattening surfaces formed on the central portion for any or all of the jaw members 20 and 24 of the staple remover 22, it only being required that pressure between those jaw members 20 and 24 and the crank-like structure thus formed in the central portion of the staple causes that central portion to be rotated to a position with the surfaces of the jaw members engaging the central portion disposed at right angles to the side surfaces of the closed staple.

Thus the claims should not be limited by the descriptions in this specification, but only by the structures and methods steps described by the language of the claims and their equivalents.

I claim:

1. In a method for inserting and removing staples with respect to living tissue or skin, comprising the steps of:
providing an open staple comprising a central portion, and end portions attached to said central portion and having pointed distal ends which project away from its central portion in a single plane;
positioning the pointed ends of the staple adjacent the tissue;
closing the staple by bending it in the plane so that its pointed ends pierce the tissue and its end portions move to a position with their pointed ends adjacent each other so that the tissue is gathered and held together by the closed staple; and
opening the staple by bending the central portion of the staple to generally a U-shape so that the end portions of the staple will retract from the tissue, which bending is caused by placing two spaced jaw members of a staple remover between the tissue and the central portion of the staple, placing a third jaw member of the staple remover between said two jaw members on the side of said central portion opposite said tissue, and manually manipulating the staple remover to move the jaw members into general alignment with each other so that the U-shaped bend is made in the central portion;
the improvement wherein said method further includes providing a crank-like structure along the central portion of the staple, which crank-like structure is adapted to receive the jaw members, and in response to pressure from the jaw member as the jaw members are initially pressed against the central portion of the staple, will first orient the staple at a predetermined position with respect to the jaw members, and will then maintain that orientation as the central portion is bent to generally a U-shape by subsequent movement of the jaw members.

2. A method according to claim 1 wherein the central portion of the staple is generally V-shaped in the plane of said end portions to provide said crank-like structure with an indentation centrally along the central portion on its side opposite the pointed ends adapted to receive the third jaw member of the staple remover, and the surfaces of the central portion adjacent the end portions are adapted to receive the two spaced jaw members.

3. A method according to claim 1 wherein said closing step is performed by a stapler including a ram adapted to close the staple by bending the staple around an anvil; and the ram and the anvil are shaped to bend the central portion of the staple to provide said crank-like structure during closing of the staple.

4. In a closed medical staple engaged with living tissue of the type comprising a central portion, and end portions attached to said central portion and having pointed distal ends, which end portions, when said staple was open, projected away from the central portion of the staple in a single plane, said staple having been closed by bending the staple in said plane so that the pointed distal ends of the staple pierced said living tissue and the end portions of the staple moved to positions with their pointed ends directed toward, aligned with and adjacent each other so that the end portions and the central portion of the staple define a generally "D" shaped single loop and said tissue was gathered and is held together by said closed staple, said staple being adapted to be opened by bending the central portion of the staple to generally a U-shape so that the end portions of the staple will retract from the tissue, which bending is caused by placing two spaced jaw members of a staple remover between the tissue and the central portion of the staple, placing a third jaw member of the staple remover between said two jaw members on the side of said central portion opposite said tissue, and manually manipulating the staple remover to move the third jaw member between the spaced jaw members so that the U-shaped bend is made in the central portion; the improvement wherein said closed staple has a crank-like structure in said central portion, which crank-like structure is adapted to receive the jaw members, and in response to pressure from the jaw members as the jaw members are initially pressed against the central portion of the staple, will first orient the staple at a predetermined position with respect to the jaw members, and will then maintain that orientation as the central portion is bent to generally a U-shape by subsequent movement of the jaw members to open said closed staple.

5. A open staple according to claim 4 wherein the central portion of the staple is generally V-shaped in the plane of said end portions to provide said crank-like structure with a central indentation along the central portion on its side opposite the pointed ends adapted to receive the third jaw member of the staple remover, and the surfaces of the central portion adjacent the end portions adapted to receive the two spaced jaw members.

* * * * *

UNITED STATES PATENT AND TRADEMARK OFFICE
CERTIFICATE OF CORRECTION

PATENT NO. : 4,802,478

DATED : February 7, 1989

INVENTOR(S) : August L. Powell

It is certified that error appears in the above-identified patent and that said Letters Patent is hereby corrected as shown below:

Col. 1, line 25, "adjacent each other" should be deleted.

Col. 3, line 29, "adjacent each other" should be deleted.

Col. 3, line 36, "U-shaped" should read --U-shape--.

Signed and Sealed this

Thirteenth Day of February, 1990

*Attest:*

JEFFREY M. SAMUELS

*Attesting Officer*       *Acting Commissioner of Patents and Trademarks*